(12) United States Patent
Berenshteyn et al.

(10) Patent No.: US 10,245,386 B1
(45) Date of Patent: Apr. 2, 2019

(54) FORCE AMPLIFIER

(71) Applicants: Annaniy Berenshteyn, Edgewater, NJ (US); Gennady I Kleyman, Brooklyn, NY (US)

(72) Inventors: Annaniy Berenshteyn, Edgewater, NJ (US); Gennady I Kleyman, Brooklyn, NY (US)

(73) Assignee: Niswey, L.L.C., Atlantic Heights, NJ (US)

( * ) Notice: Subject to any disclaimer, the term of this patent is extended or adjusted under 35 U.S.C. 154(b) by 68 days.

(21) Appl. No.: 15/298,310

(22) Filed: Oct. 20, 2016

(51) Int. Cl.
*A61M 5/20* (2006.01)
*A61M 5/315* (2006.01)

(52) U.S. Cl.
CPC .......... *A61M 5/31576* (2013.01); *A61M 5/20* (2013.01); *A61M 5/31515* (2013.01); *A61M 2005/2026* (2013.01); *A61M 2005/3152* (2013.01)

(58) Field of Classification Search
CPC .............. A61M 5/31576; A61M 5/20; A61M 5/31515; A61M 2005/2026; A61M 2005/3152; A61M 5/31578; A61M 5/3158; A61M 5/31583; A61M 5/31585; F16H 25/20; F16H 2025/2059; A61B 17/8822; A61B 17/8825; A61B 17/00491; A61B 2017/00495
See application file for complete search history.

(56) References Cited

U.S. PATENT DOCUMENTS

| | | | | |
|---|---|---|---|---|
| 4,857,056 A | * | 8/1989 | Talonn | A61M 5/1454 604/135 |
| 2015/0328405 A1 | * | 11/2015 | Metzner | A61M 5/20 604/143 |
| 2016/0296706 A1 | * | 10/2016 | Blancke | A61M 5/31551 |

* cited by examiner

*Primary Examiner* — Nathan R Price
*Assistant Examiner* — Dung T Ulsh (57) ABSTRACT

A force multiplier having a substantially non-rotating input screw to which a force to be amplified is applied relative to an external housing, a substantially non-rotating output screw providing a resulting output force relative to the housing, and a rotating nut disposed to receive and engage each of the input screw and the output screw and disposed to engage the housing and provide a force opposite to the output force, wherein the output screw is movable in a first direction when the input force is applied and is retractable upon relief of the input force, and an advancement ratchet disposed to engage the output screw and receive the output force relative to the housing having an output member providing a monotonically increasing motion in response to a plurality of cycles of force multiplier output screw first direction advancement and retraction. Also included is a mating syringe.

5 Claims, 7 Drawing Sheets

FORCE AMPLIFIER

FIELD OF THE INVENTION

The present invention relates to mechanical force amplifiers, in particular to mechanical force amplifiers having linear actuation.

BACKGROUND OF THE INVENTION

Regular syringes that do not have a force-amplification structure are typically held by the user between the index and middle fingers whereas the thumb applies a linear force to the syringe plunger over a distance. When significant forces are not required, such a syringe is associated with accurate aiming of the substance to be dispensed and full control of the dispensing, since the motion of the thumb coincides with the line of the plunger's movement.

However, the dispensing of sticky and/or viscous materials from a syringe requires the application of a significant force to the plunger of the syringe. Depending on the viscosity of the dispensed material and the amount of this material, the user may experience difficulties in generating, maintaining and/or controlling such a force for the necessary period of time. As a consequence, an inadequate or poorly controlled force and/or the user's fatigue results, particularly when a need arises to use a syringe repetitively, lead to undesirable, inaccurate results.

Some devices operative to amplify an input force are configured with a pistol-type handle having an attached lever which amplifies the force of the person's hand and applies it to the plunger of a syringe. During the use of such a pistol-type force amplifying device with a syringe, the line of movement of the plunger is located above the user's hand, and the distribution of substance exiting from the syringe occurs when the user squeezes the lever of the syringe force amplifying device. This configuration does not allow accurate aiming of the substance and hampers dispensing, especially in applications where such a delivery of substance occurs in tight areas with limited visibility. These conditions can be encountered in numerous industries including, but not limited to, medical procedures, such bonding fractured bones or cementing ruptured spinal disks, as well as soldering paste dispensing in fabrication of electrical and electronic equipment.

Also known is a force amplifying device that engages a syringe in-line with the syringe wherein the length of the driving member of this device must be equal to the length of the syringe plunger rod or longer in order for the syringe-engaging rod plunger to travel the entire [content containing] length of the syringe barrel and to expel all of the substance from it, adding significant size to the combination of the syringe and force amplifying device, so that the whole arrangement substantially long, typically unnecessarily impeding the precise positioning of the syringe tip prior to and during substance dispensing.

It is, therefore, desirable to have a simple force amplifier configured to provide accurate and convenient dispensing of substance while not requiring the exertion by the user of significant loads along the user axis of motion.

SUMMARY

The present invention provides a force multiplier having a substantially non-rotating input shaft to which a force to be amplified is applied relative to an external housing, a substantially non-rotating output shaft providing a resulting output force relative to the housing, and a rotating nut disposed to receive and engage each of the input shaft and the output shaft and disposed to engage the housing and provide a force opposite to the output force, wherein the output shaft is movable in a first direction when the input force is applied and is retractable upon relief of the input force, and an advancement ratchet disposed to engage the output shaft and receive the output force relative to the housing having an output member providing a monotonically increasing motion in response to a plurality of cycles of force multiplier output shaft first direction advancement and retraction. When connected to a syringe, the embodiment of the present invention provides the output force to the syringe input rod in response to a force substantially along the syringe and syringe rod axis, to provide a significant and selectable reduction in force necessary to dispense material from the syringe while providing a minimal extension to the axial length of the syringe (or other connected devices).

BRIEF DESCRIPTION OF THE DRAWING

These and further features of the present invention will be better understood by reading the following Detailed Description, taken together with the Drawing figures, wherein.

DETAILED DESCRIPTION

Figure 1:
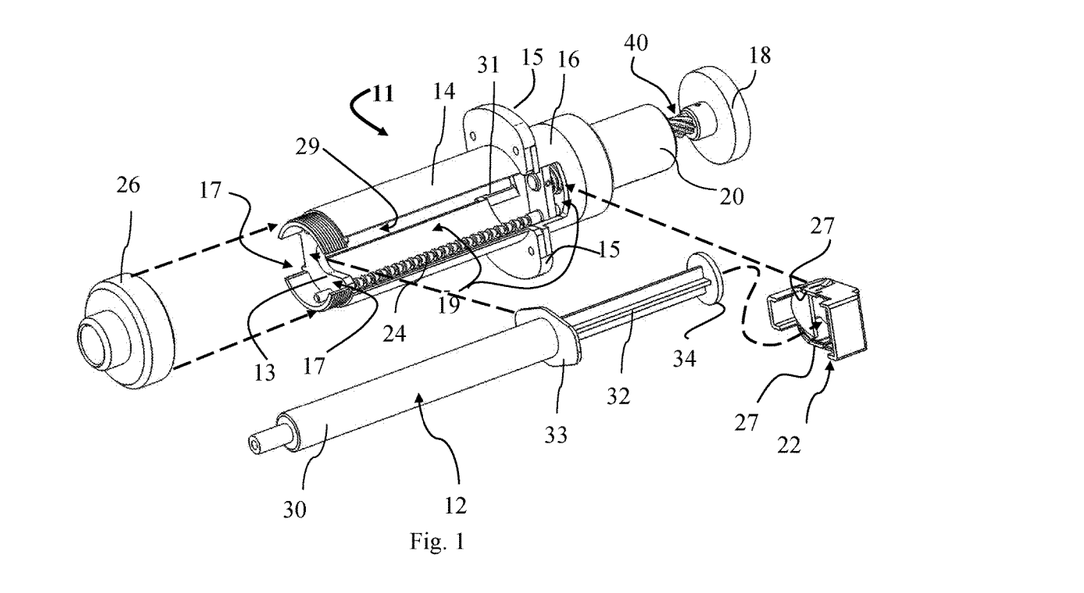
FIG. 1 is a partially exploded perspective view of one embodiment of the invention showing the Syringe, the Force Transmitting Unit, the Syringe Attachment Nut, and the Syringe Rod Adapter the device.

An embodiment 11 of the present invention is shown in FIG. 1, includes a front housing 14 which receives a portion of a typical syringe 12 including a syringe adapter 22 attached to the syringe push rod, and being retained in the front housing 14 by threaded cover 26 placed over the syringe barrel 30 retaining its flanges 33 against a wall 13. When the syringe 12, alone, is typically operated in the hand of a user, the user grasps the syringe barrel 30 flanges 33 and pushing the push rod 32 end 34 toward the flanges 33. The embodiment 11 of FIG. 1 by comparison provides the user with force amplifier flanges 15 to grasp and knob 18 to push against to provide the desired dispensing of syringe material. The force amplifier 11 according to one embodiment of the present invention includes the front housing 14, a back housing 16 and a bearing housing 20 which having the force amplification mechanism. The front housing 14 receives the syringe 12 flanges 33 against a wall 13, push rod 32 and end 34, and bearing housing retains a push knob 18 connected to direct user-applied force into the force amplifier 11 internal mechanism (described below) via input screw 40. In operation, the user provides repeated application of force to button 18 relative to the flanges 15 whereinafter each application of force, the knob 18 returns to it prior, undepressed position, and the internal force amplification mechanism and ratchet mechanism according to the present invention provides a unidirectional motion to the syringe 12 push rod 32 end 34.

Figure 2:
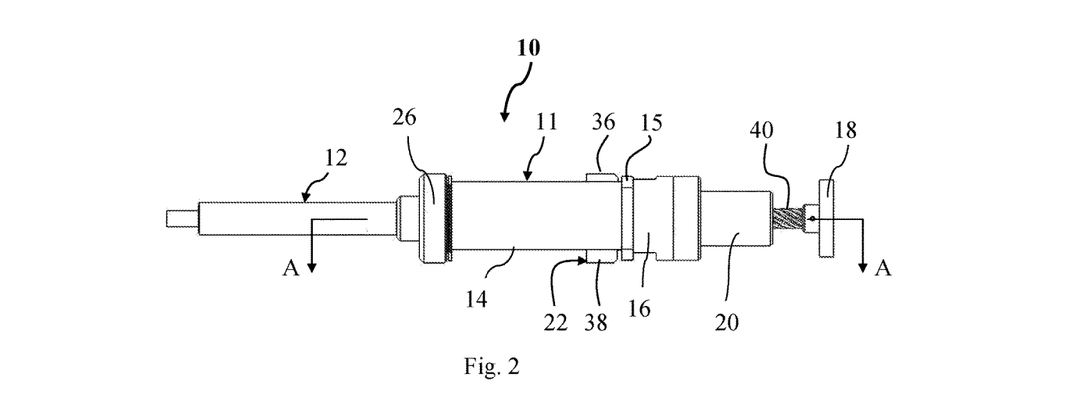
FIG. 2 is a plan view of the embodiment of FIG. 1.

When the elements of the embodiment of the present invention 11 and the syringe 12 are assembled, a force-amplified syringe assembly 10 is provided and shown in the plan view of FIG. 2, where the syringe 12 is shown extending from the front housing 14 to which it is retained by the proximal end of the threaded cover 26 (now fully seated on the threaded end of front housing 14), while the push rod end (34) is retained by adapter 22 in turn retained within longitudinal slots 29, 19 (FIG. 1) the front housing 14, the adapter 22 keyed ends 36, 38 being visible in FIG. 2.

Figure 3:
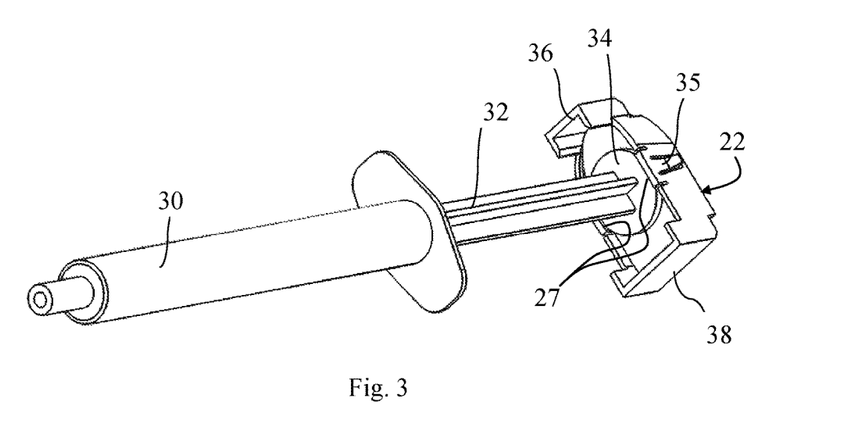
FIG. 3 is a perspective of the Syringe with the Syringe Rod Adapter attached.

The syringe adapter 22 is shown in greater detail in FIG. 3, wherein the syringe 12 push rod 32 end 34 is permanently or removably received into the adapter 22 and retained by inwardly facing protrusions 27 and adapter 22 sides. The adapter 22 is preferably made out plastic by means of injection molding and includes laterally extending (radially outward from the retained position of the end 34) extensions or keys 36, 38 wherein the keys 36, 38 may respectively comprise a narrow key and a relatively broader key to fit within correspondingly narrow and broader slots 29, 19 respectively, to provide unambiguous alignment of the adapter (and thus the end 34) within the front housing 14 in preparation to receive force thereon from the force amplification mechanism described below. The force is applied to the syringe end rod 34 and advances (and thus dispensing material from the syringe) from the adapter 22 via the adapter resilient ratchet arms 35, 37 which extend outwardly from the sides of the adapter 22 generally orthogonal to the direction that the keys 36, 38 extend permitting easy lateral insertion and engagement of the ratchet arms 35, 37 with corresponding ratchet shafts 25, 24 (FIGS. 1, 4-6), which may be described as formed with the series of grooves, with one side of each groove being substantially vertical and the other being substantially inclined, and the distance between the identical features of the adjacent grooves corresponds to the displacement of the Syringe Rod 32 per every activation of the device. When the desired amount of material is dispensed from the syringe 12, the threaded cover 26 may be removed, the syringe 12 removed, and the adapter 22 may be removed from the rod 32 end 34 for re-use, or the entire assembly 10 (FIG. 2) may be discarded. Alternate embodiments include a syringe with integrated end and adapter having the features according to the present invention.

Figure 4:
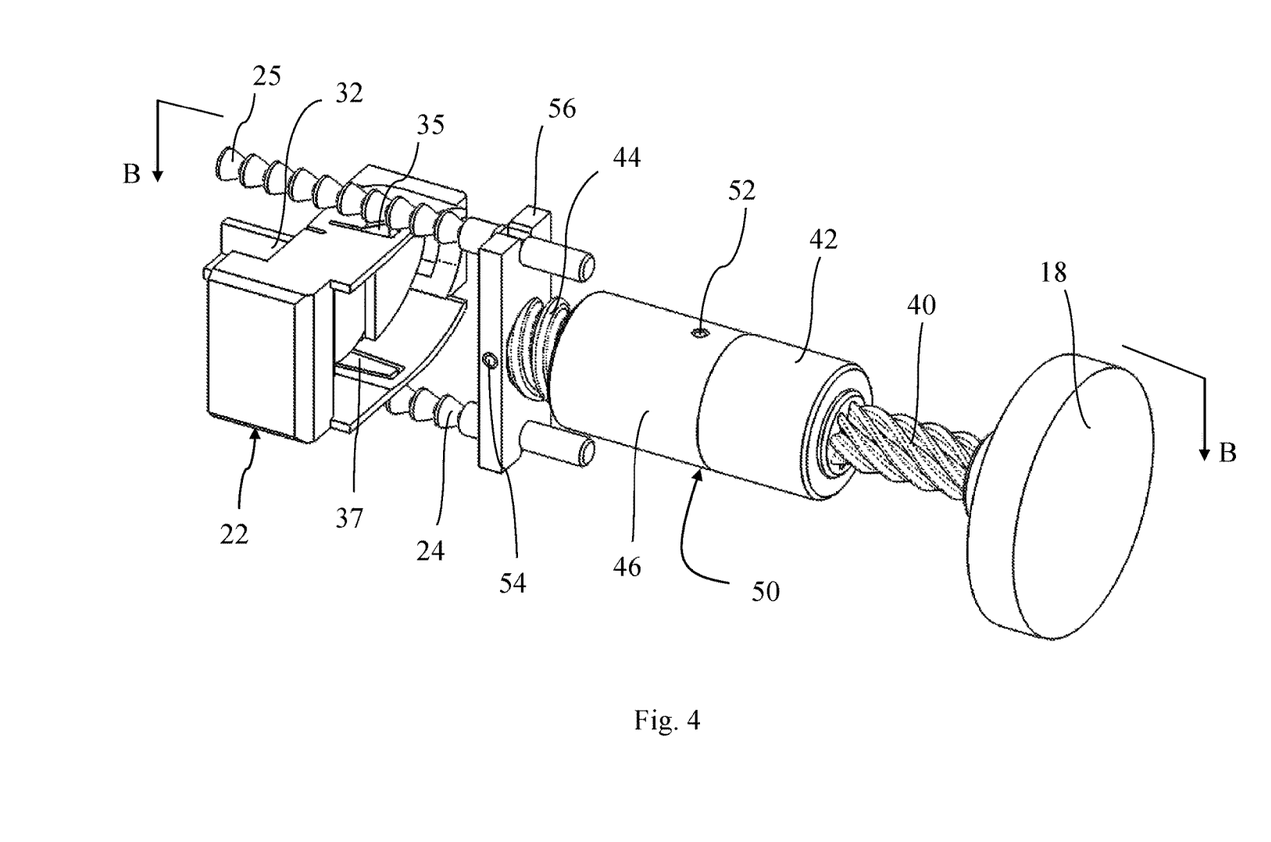
FIG. 4 is a partial perspective view of the embodiment of FIG. 1 with Front Housing 14, Back Housing 16, and Bearing Housing 20 removed.
Figure 5:
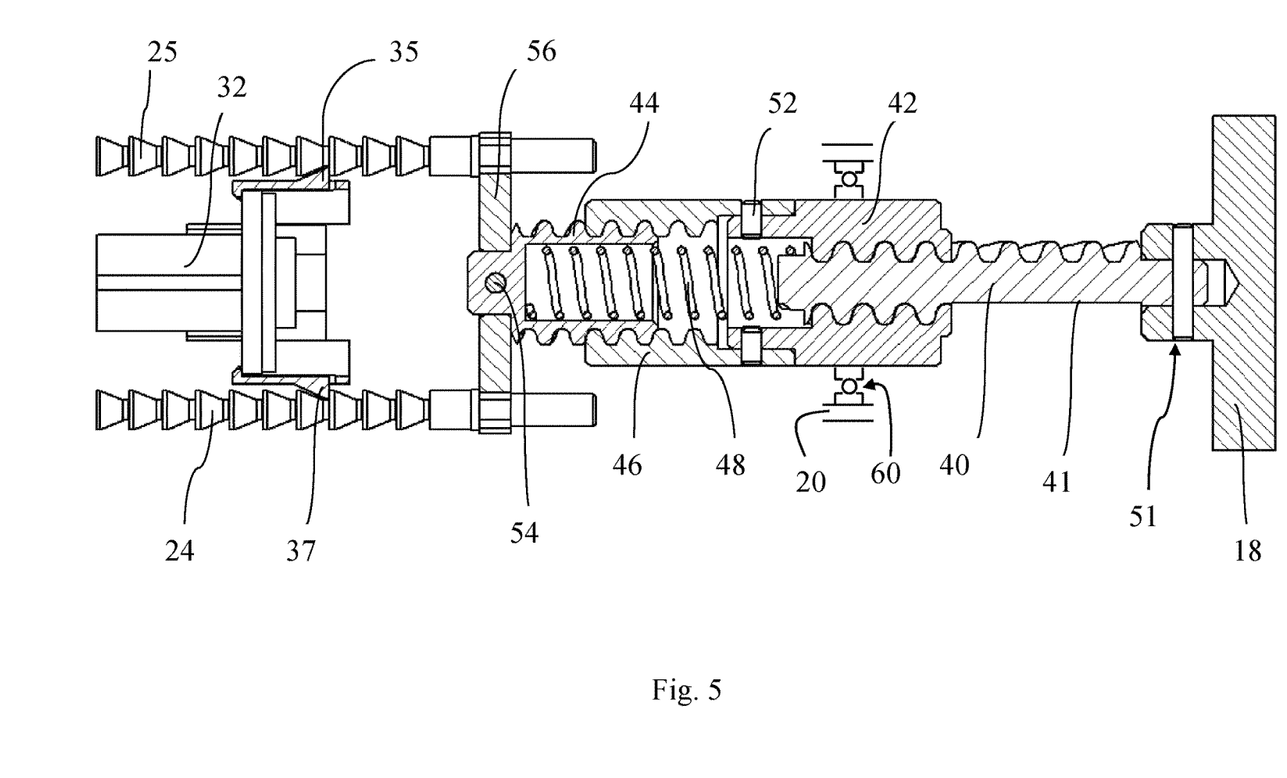
FIG. 5 is a cut-away view of an embodiment of FIG. 4 of the present invention long lines B-B with a bearing added.

A perspective view of the force amplification mechanism typically retained within bearing housing 20 attached to the back housing 16 (FIGS. 6-7) and applicable to the embodiment described herein is shown in FIG. 4 and in cross-section of FIG. 5 taken along section B of FIG. 4, wherein a force translation nut 50 includes an input end 42 having an axial opening with a thread having a pitch to receive threaded input screw 40 which provides a force from knob 18, wherein the input screw 40 is substantially non-rotating with reference to the bearing housing 20 while it may move in and out of a bearing housing aperture. The force translation nut 50 is restrained from axial movement (along the length of the bearing housing 20) e.g. by bearing 60 secured thereto, and/or by forward wall 23 and bearing housing end wall 21, resulting in the force from the input screw 40 inducing the input end 42 (and entire nut 50) to rotate relative to the bearing housing 20 at a rate (degree of rotation-to-input distance change) dependent on the screw 40 thread pitch. The force translation nut 50 includes an output end 46, rotationally fixed to the input end 42 e.g. by pin 52 or otherwise, and is adapted to receive an output screw 44 into mating threads having a pitch less than the thread pitch of the input end 42 and screw 40, wherein both input screw 40 and output screw 44 have the same thread 'handedness' (both either have right-hand thread or left-hand thread). The force applied to the knob 18 results in the inward (relative to the nut 50) motion causing force translation nut 50 to rotate an amount corresponding to the input nut 42 thread pitch which rotation causes the output end 46 to rotate on the output screw 44, having a thread pitch less than the input screw, moves out of (or away from) the nut 50 at a rate more slowly than the rate the input screw 40, preferably restrained from rotation, but at a greater (amplified) force to subsequently connected devices, e.g. the syringe 12. If some rotation of either or both the input or output shafts 40, 44 is permitted, nut 50 rotation and screw 40 and screw 44 forces will be correspondingly affected. Thus, the ratio between the travel distances of the input screw and the output screw is inversely proportional to the ratio between the force applied to the input screw 40 by the operator and the force produced by the output screw 44 (which is ultimately applied to the Syringe Rod 32). In one of the preferred embodiment of the invention the ratio between the screw pitches (and corresponding travel distances) of the output screw 44 and the input screw 40 is 1:5, which results in five-fold increase (typically slightly less when friction losses are taken into account) of the output force. Moreover, as the input force is proportional to the output force, the operator can sense a change in syringe material characteristic that may be reflected in a change in required syringe dispensing force.

Figure 6:
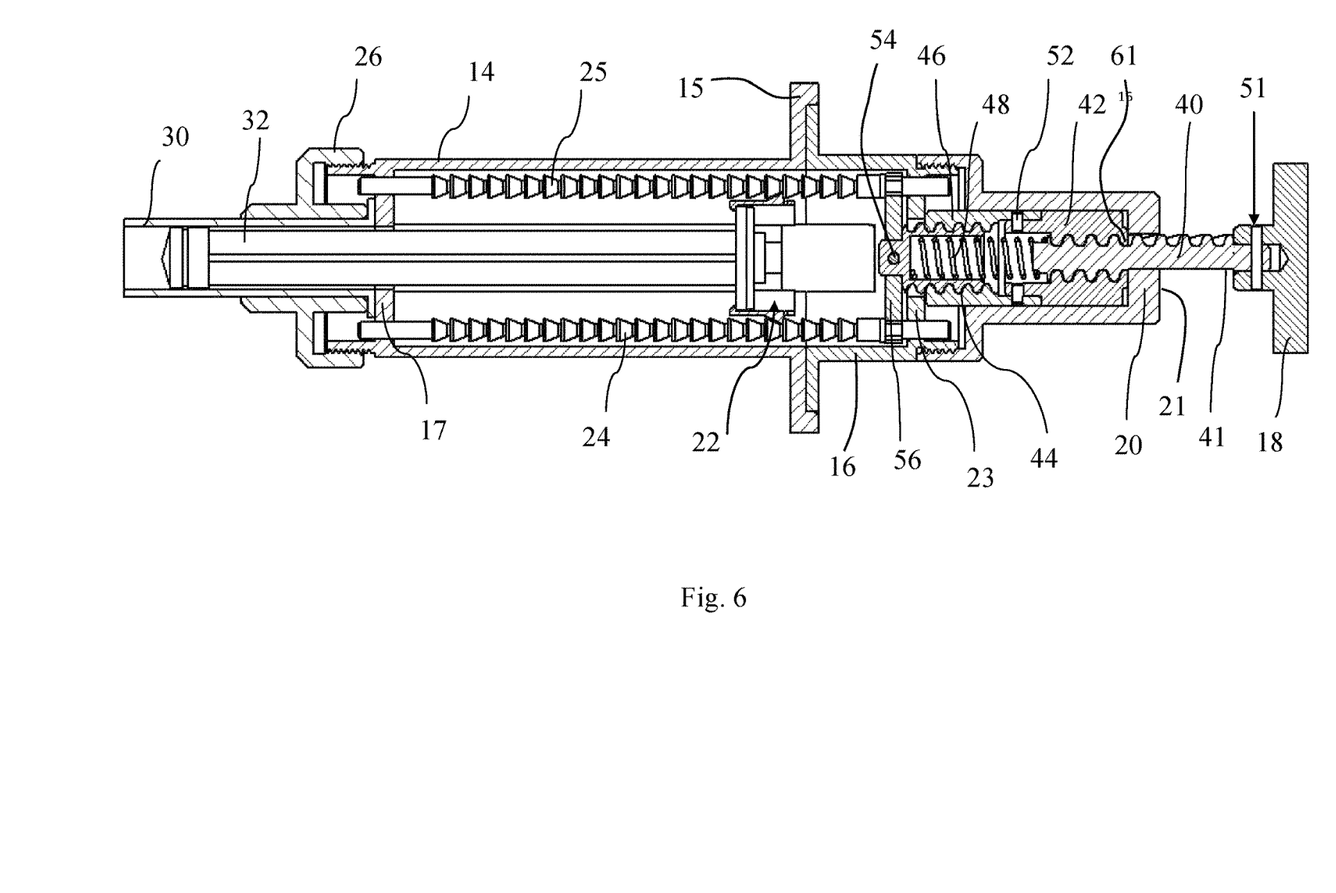
FIG. 6 is a cross-sectional side view of the embodiment of FIG. 1 cut along lines A-A on FIG. 2 at a quiescent state of the device.
Figure 7:
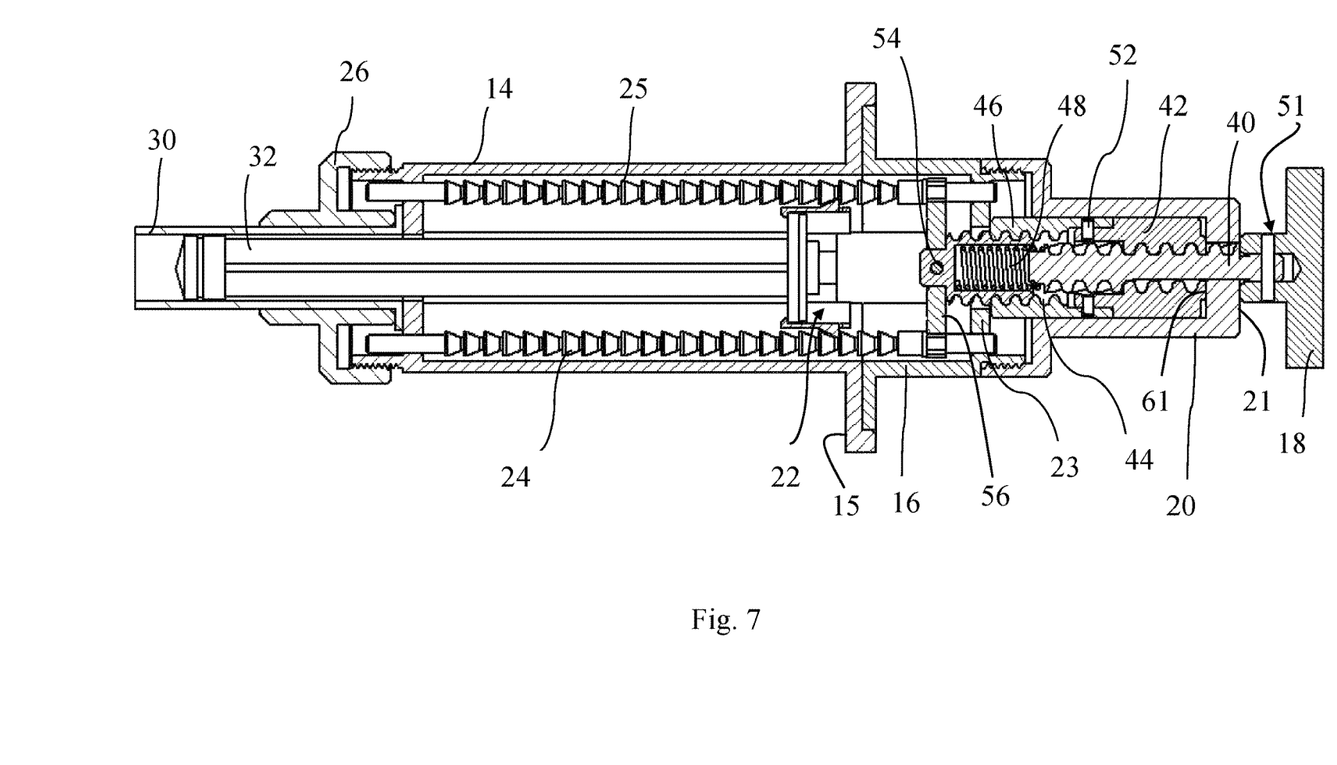
FIG. 7 is a cross-sectional side view of the embodiment of FIG. 1 cut along lines A-A on FIG. 2 at a fully force compressed state of the device.

In one embodiment, when the user stops pushing and releases the knob 18, the force translation nut 50 is induced to turn in a reverse direction (relative to the above operation) by retraction of the input screw, resulting in a corresponding retraction in the output screw 44 and force provided therefrom. In the embodiments of FIGS. 5-7, when a spring 48, internal to the force translation nut 50, is compressed by moving the input shaft 40 into the nut 50, the spring 48 urges the input shaft to move outward from the nut 50 so that when the knob 18 is released by the user, the thread between the input screw 40 and the input end 42 causes reverse rotation of the force translation nut 50 as the spring 48 moves the shaft 40 out of the force translation nut 50. In this particular embodiment, the input and output screws 40, 44 do not rotate with respect to each other, making an attractive anchor for the ends of the spring 48. In compact embodiments, a recess in one or both screws 40, 44 may be provided to accommodate the desired spring 48 compression and extension dimensions.

In the embodiment shown, the force provided by the output screw 44 is received by a link 54 attached to the output screw 44 by pin 54 extending radially outward to engage and transfer output screw 44 force to ratchet shafts 24, 25 which generally extend along the interior of the front housing 14, and in the present embodiment, extend through an apertures (or equivalent) in the wall 13 and wall 23 to maintain a substantially parallel separation, favoring reliable engagement of ratchet arms 35, 37 along the ratchet shafts 25, 24 which by their connection to link 54, together move axially in unison as the output screw 44 moves axially, and correspondingly providing the force from the output screw 44 to the adapter 22 radially pliant ratchet arms 35, 37. The ratchet shafts 24, 25 and ratchet arms 37, 35 engage to limit relative motion when the ratchet shaft or ratchet arm (and in this embodiment the output shaft 44 or adapter 22) is urged toward the other by a force, while relative motion of separation of the link 56 and adapter 22 is permitted. In this embodiment, the ratchet shaft 24, 25 have longitudinally (vertical) walls substantially perpendicular to the axis of each ratchet shaft 24, 25 alternating with surfaces sloping from an outer diameter toward the axis of each ratchet shaft 24, 25. In the particular embodiment shown, the sloping surfaces substantially comprise a conical shape. The ratchet arms 35, 37 each have a surface extending substantially perpendicular to the axis on which the syringe 12 rod 32 moves and are disposed to engage a corresponding substantially perpendicular ratchet shaft 25, 24 surface sufficient to transfer force from said output screw 44 (via link 56) to said syringe 12 end 34 (via adapter 22) to cause the dispensing of material from the syringe 12 barrel 30. The ratchet arms 35, 37 typically have a sloped surface adjacent their perpendicular surfaces, but other mating surfaces having unidirectional engagement of relative motion of the parts are within the scope of the present invention. Upon reverse motion of the ratchet shafts 24, 25, the surfaces of either or both the ratchet shafts 24, 25 or ratchet arms 37, 35 slide over each other aided by the sloped surfaces of either or both ratchet shafts and ratchet arms at least sufficient to allow the ratchet arms 35, 37 to engage a different ratchet shaft perpendicular surface to further advance the rod 32 end 35 toward the treaded cover 26 upon a repeated advance of the knob 18 from force applied thereto.

Cross-sectional views taken along the section A of FIG. 2 of an embodiment according to the present invention in a released state and prior knob-compressed state are shown in FIGS. 7 and 6 respectively, wherein FIG. 7 shows the ratchet arms (and movable elements connected thereto) being disposed to the left (threaded cover 26 side) extreme of their travel as a result of completion of the application of force on the knob 18, wherein the adaptor 22 ratchet arms 35, 37 engage the $4^{th}$ perpendicular surface of each ratchet shaft 25, 24. Upon release of the knob 18 by the user, the screw 40 is urged out of the input end 42 by spring 48, causing reverse rotation of the force translation nut 50 and corresponding retraction of link 56 and both ratchet shafts 24, 25 shown in FIG. 6, allowing each ratchet arm 37, 35 to engage a new (i.e. the $5^{th}$) perpendicular surface of the corresponding ratchet shaft 24, 25 as the syringe 12 rod 32 end 34 and connected adapter 22 typically remain in position as the ratchet shafts 35, 37 retract. The process continues with subsequent sequence of applications of force and release of knob 18, wherein further (e.g. $6^{th}$, $7^{th}$, etc.) vertical surfaces are engaged, moving the syringe push rod 32 end 34 into the syringe body thus dispensing the syringe 12 material.

In the embodiments of FIGS. 6 and 7, the bearing 60 of FIG. 5 is replaced by an input end 42 raised shoulder 61 which confronts and moves over a bearing housing 20 end wall 21 inner surface as an alternate bearing also transmitting the amplified force. In one embodiment, the force in opposition to the output screw 44 force, is seen as the force from the body of the translation nut 50 transferred via bearing 60 or surface 61 to bearing housing 20 and thus to the syringe 12, minus the force applied to the button 18, according to the present invention.

Figure 8:
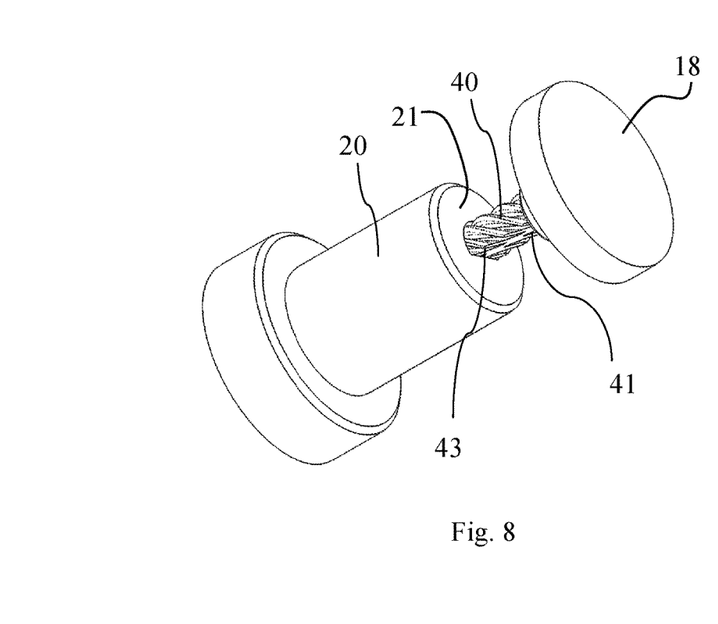
FIG. 8 is a partial perspective view of the proximal end of the embodiment of FIG. 1.
Figure 9:
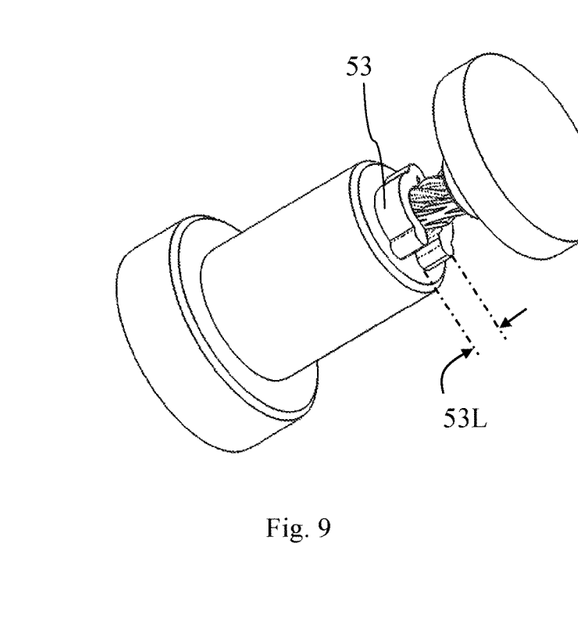
FIG. 9 is a partial perspective view of an alternate embodiment of the present invention.

In one embodiment of the present invention shown in FIG. 8, the input shaft 40 is made substantially rotationally fixed relative to the bearing housing 20 by an end wall 21 opening flat section 43 and a corresponding input screw 40 flat section 41, allowing the input shaft to move into and out of the bearing housing 20 while preventing substantially any relative rotation of the screw 40. Moreover, the knob 18 may also be fixed to the screw 40 and rotationally fixed relative to the bearing housing 20 by a shaft flat spot and/or pin connection 51, providing the user with confident positioning and predictable operation. A removable or fixed stroke spacer 53 may also be added according to the embodiment of FIG. 9 having a length 53L providing improved selective metering of material dispensed from the syringe according to the present invention. The stroke spacer of a desired length 53L is interposed between the knob 18 and end wall 21, typically at least partially surrounding the input screw 40.

The embodiments and scope of the preset invention also include other applications and structures requiring the application of a force over a distance, and according to the present invention, the connecting elements, e.g. the adapter 22, front housing 14, etc. may be adapted to provide appropriate interconnection and force transfer. Further modifications and substitutions made by one of ordinary skill according to the present invention are within the scope of the present invention, which is not to be limited, except by the claims that follow.

What is claimed is:

1. A linear force amplifier, comprising:
a housing having a length;
a force multiplier having an input screw substantially non-rotating relative to said housing and having an axis, to which an input force to be amplified is applied relative to said housing, an output screw substantially non-rotating relative to said input screw, providing a resulting output force relative to said housing, and a rotating nut rotatable about said input screw axis and disposed to receive and engage each of said input screw and said output screw and disposed to engage said housing and provide a force to said housing opposite to said resulting output force, wherein said output screw is movable in a first direction when said input force is applied and is retractable opposite said first direction upon relief of said input force;
an advancement ratchet disposed to engage said output screw and receive said output force relative to said housing having an output member providing an increasing ratchet output member displacement in said first direction in response to a plurality of cycles of force multiplier output screw motion in said first direction advancement and retraction therefrom.

2. The linear force amplifier of claim 1, wherein said rotating nut has threads of different pitches but both either are right-hand or left-hand threads, which said rotating nut threads correspondingly engage mating threads of each of said input screw and said output screws.

3. The linear force amplifier of claim 1, wherein said advancement ratchet includes a plurality of spaced shafts each extending along a length and each have a sequence of axially tapering segments disposed along said ratchet shaft length.

4. The linear force amplifier of claim 3, wherein said advancement ratchet further includes an adapter disposed proximal said plurality ratchet shafts having resilient members extending therefrom and being disposed to engage said spaced shafts and providing a monotonically increasing said displacement.

5. The linear force amplifier of claim 1, wherein
said adapter is connected to a movable rod of a syringe, and
said housing retains said syringe.

* * * * *